(12) United States Patent
Yu et al.

(10) Patent No.: US 7,876,950 B2
(45) Date of Patent: Jan. 25, 2011

(54) IMAGE CAPTURING FOR PATTERN RECOGNITION OF ELECTRONIC DEVICES

(75) Inventors: Wei Yu, Hong Kong (HK); Mei Kwong Cheng, Hong Kong (HK); Hon Shing Law, Hong Kong (HK)

(73) Assignee: ASM Assembly Automation Ltd, Hong Kong (HK)

( * ) Notice: Subject to any disclaimer, the term of this patent is extended or adjusted under 35 U.S.C. 154(b) by 1177 days.

(21) Appl. No.: 11/469,996

(22) Filed: Sep. 5, 2006

(65) Prior Publication Data

US 2008/0056560 A1    Mar. 6, 2008

(51) Int. Cl.
    *G06K 9/00* (2006.01)
(52) U.S. Cl. ............... 382/141; 382/181; 382/190; 348/86; 348/91
(58) Field of Classification Search ........... 382/100, 382/141–152, 181, 190–196; 348/86–87, 348/91–92
See application file for complete search history.

(56) References Cited

U.S. PATENT DOCUMENTS

| | | | | |
|---|---|---|---|---|
| 6,177,682 | B1 * | 1/2001 | Bartulovic et al. | 250/559.44 |
| 6,222,935 | B1 * | 4/2001 | Okamoto | 382/149 |
| 6,700,122 | B2 * | 3/2004 | Matsui et al. | 250/310 |
| 2002/0196336 | A1 * | 12/2002 | Batson et al. | 348/86 |
| 2004/0156054 | A1 | 8/2004 | Christoph | 356/601 |

OTHER PUBLICATIONS

Chinese Office Action mailed Jun. 19, 2009 in corresponding Chinese Patent Application No. 2007101460159.

* cited by examiner

*Primary Examiner*—Manav Seth
(74) *Attorney, Agent, or Firm*—Ostrolenk Faber LLP

(57) ABSTRACT

An image capturing method and apparatus for pattern recognition of an electronic device are provided in which an electronic device is moved relative to a vision system for positioning the vision system over a target position on the electronic device, and when the vision system is positioned to view the target position, the vision system is operative to capture an image of the target position while the electronic device is undergoing relative motion with respect to the vision system without stopping. Thus, the time taken for pattern recognition can be significantly reduced.

19 Claims, 5 Drawing Sheets

180; # IMAGE CAPTURING FOR PATTERN RECOGNITION OF ELECTRONIC DEVICES

FIELD OF THE INVENTION

The invention relates to the capturing of images of multiple positions on electronic devices during processing, such as alignment prior to performing bonding on the electronic devices, and in particular to pattern recognition (PR) alignment.

BACKGROUND AND PRIOR ART

In the semiconductor assembly and packaging industry, it is usually necessary to electrically connect different electronic devices, such as an integrated circuit chip or die to a substrate on which it is mounted by bonding. Such electrical connections can be done using conductive wires or direct connection between conductive pads. The bond pads on the electronic devices have to be aligned with respect to a bonding tool that is used for performing bonding.

For example, in wire bonding, the positions of the bond pads must first be determined prior to bonding conductive wires onto the bond pads. A vision system is typically used to capture images of an electronic device for alignment of its bond pads. The substrate to be bonded is placed onto a worktable, which is in turn mounted on a positioning stage such as an XY table. The positioning stage moves the electronic device relative to the vision system to capture images of predetermined points on the substrate for PR alignment. Sometimes, it is possible for the vision system to look for several position indicia on the electronic device, and use these to calculate the positions of all the bond pads on the electronic device if they are of a fixed pattern. In other cases, calculating bonding positions from selected position indicia may not offer enough precision, and each bonding position on each bond pad has to be recognized. One example is an LED device, wherein the bonding positions are scattered in dot matrix form over a substrate to be bonded, and each bonding position preferably should be individually recognized during PR alignment.

For bonding applications in general, the total bonding time would usually consist of: (1) loading and unloading of materials, (2) PR alignment, and (3) actual bonding. Where there are a large number of discrete bonding positions, such as for LED bonding, the PR alignment time occupies a significant portion of the total bonding time. Saving PR alignment time would be one major factor in improving the productivity of the bonding apparatus.

In terms of processing time, conventional PR alignment methods take up much time because a positioning stage needs to stop the electronic device at each bonding position relative to the vision system for camera exposure so that the vision system is able to capture images of the bonding positions to thereby align the bonding points. Thus, to move from point to point for PR alignment, the positioning stage needs to go through acceleration and deceleration for each change of position, not including the time spent when the electronic device is stationary. This method is time-consuming.

FIG. 1 is an illustration of a typical motion sequence showing the points at which PR image-grabbing is performed in a prior art PR alignment system. The motion velocity-time graph 10 approximates the motion of the positioning stage to position bonding positions of the electronic device relative to a vision system. The PR grab graph 12 indicates when an image of a bonding position is acquired. The graphs illustrate that at trough positions 14 when the positioning stage stops the electronic device at a bonding position, the vision system grabs an image of the bonding position at the same time 16. Therefore, the positioning stage needs to accelerate and decelerate in between adjacent bonding positions whereat the positioning stage is stopped for image-grabbing.

FIG. 2 is an illustration of a prior art PR alignment method wherein LED bonding positions 18 are moved relative to a vision system from point to point. It shows a row of LED bonding positions 18 which are regularly spaced apart. The positioning stage follows a motion sequence 20 to move from one LED bonding position 18 to another and stops at the position of each and every LED bonding position 18 for an image of the bonding position to be captured.

One way to reduce the effects of the long PR alignment time is to incorporate dual worktables holding separate electronic devices so that PR alignment can be performed on one electronic device while bonding is simultaneously being performed on another electronic device. However, such an approach is not cost-effective and may introduce control complexities in having to synchronize the worktables during simultaneous PR alignment and bonding.

The long exposure time required when using conventional PR alignment methods is a bottleneck during the PR alignment process. Since the wasted time that the electronic device is stationary is a major contributing factor to PR alignment time, whereas image-grabbing as such takes considerably less time, it would be advantageous to reduce the amount of time spent on accelerating and decelerating movement of the electronic device between bonding points. The table motion time is significantly longer when the table needs to stop at every point, as compared to when the table just passes through all the points at full speed. Accordingly, if PR alignment could be performed while avoiding the need to stop at each and every bonding position to capture an image of the bonding position, PR alignment time could be significantly reduced along with total processing time of the electronic device.

SUMMARY OF THE INVENTION

It is thus an object of the invention to seek to avoid the aforesaid disadvantages of prior art PR alignment methods by minimizing the need to continuously stop the motion of the electronic device at each and every bonding position.

It is another object of the invention to seek to move the electronic device relative to a vision system for PR alignment through multiple bonding positions at a higher speed as compared to conventional PR alignment methods, hence improving productivity.

According to a first aspect of the invention, there is provided an image capturing method for pattern recognition of an electronic device, comprising the steps of: moving an electronic device relative to a vision system for positioning the vision system over a target position on the electronic device; determining when the vision system is positioned to view the target position; and then capturing of an image of the target position with the vision system while the electronic device is undergoing relative motion with respect to the vision system without stopping.

According to a second aspect of the invention, there is provided an apparatus for capturing an image for pattern recognition of an electronic device, comprising: a vision system for capturing images of the electronic device; and a positioning stage for positioning the electronic device relative to the vision system in order for the vision system to view a target position on the electronic device; wherein the vision system is operative to capture an image of the target position while the electronic device is undergoing relative motion with respect to the vision system without stopping.

It will be convenient to hereinafter describe the invention in greater detail by reference to the accompanying drawings. The particularity of the drawings and the related description is not to be understood as superseding the generality of the broad identification of the invention as defined by the claims.

BRIEF DESCRIPTION OF THE DRAWINGS

Examples of apparatus and methods for PR alignment in accordance with the invention will now be described with reference to the accompanying drawings, in which.

DETAILED DESCRIPTION OF THE PREFERRED EMBODIMENT OF THE INVENTION

Figure 1:
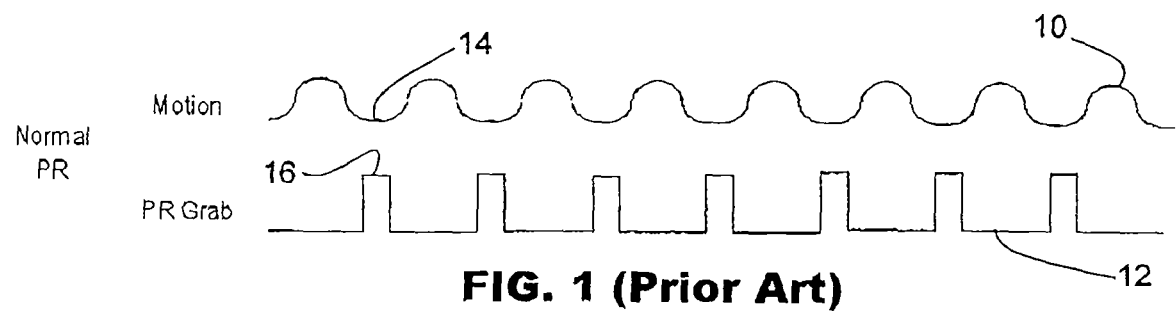
FIG. 1 is an illustration of a typical motion sequence showing the points at which PR image-grabbing is performed in a prior art PR alignment system.
Figure 2:
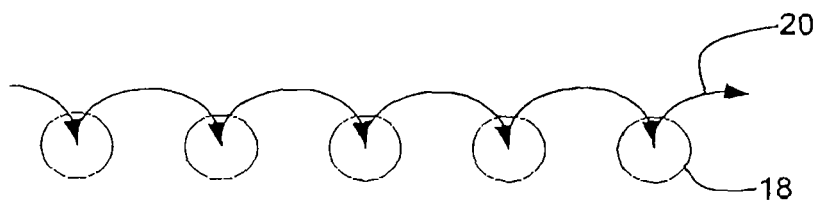
FIG. 2 is an illustration of a prior art PR alignment method wherein LED bonding points are moved relative to a vision system from point to point.
Figure 3:
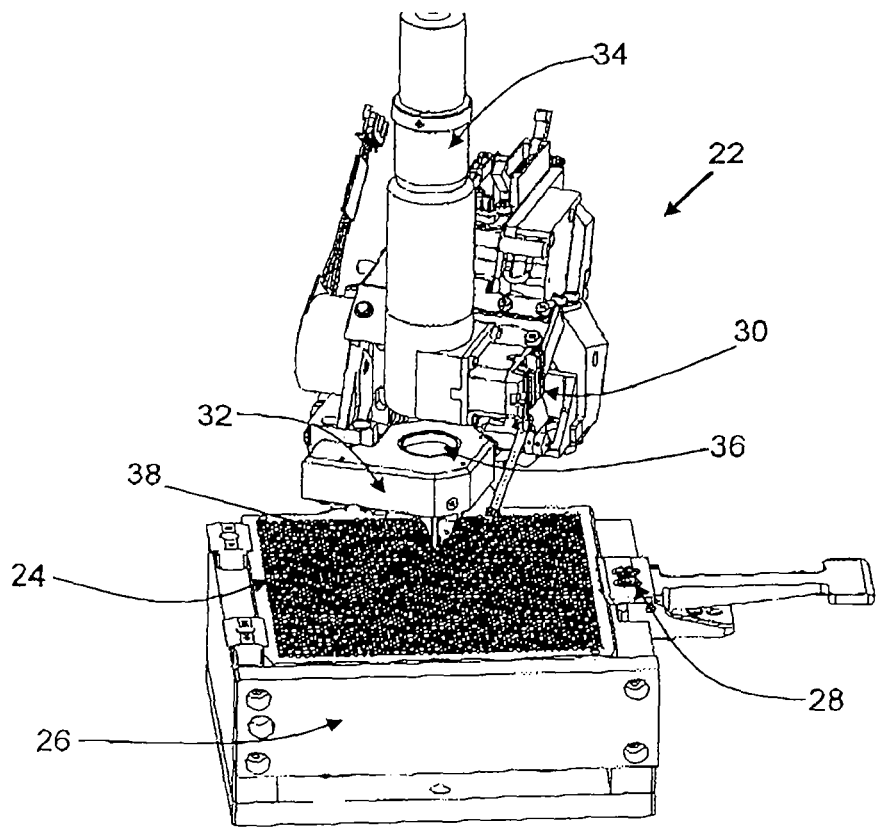
FIG. 3 is an isometric view of a wire bonding apparatus that incorporates a PR alignment apparatus and method according to the preferred embodiment of the present invention.

FIG. 3 is an isometric view of a wire bonding apparatus 22 that incorporates a PR alignment apparatus and method according to the preferred embodiment of the present invention. The bonding apparatus 22 is positioned over an electronic device, which may be in the form of a substrate 24 to be bonded. The substrate 24 is secured onto a worktable 26 that is preferably mounted on a positioning stage such as an XY table. The XY table is operative to move the substrate 24 relative to the bonding apparatus 22.

The bonding apparatus 22 has a vision system generally comprising a high intensity lighting source such as a coaxial lighting source 30, a ring lighting source 32, and a CCD camera 34 that is connected to an image grabber board. As the coaxial lighting source 30 and CCD camera 34 are located over the ring lighting source 32, a hole 36 is preferably formed in the ring lighting source 32 for illuminating a target position on the substrate 24 and for grabbing an image of the illuminated target position respectively. There is also a bonding tool 38 located on the bonding apparatus 22 for bonding conductive wires onto the substrate 24 after completion of PR alignment.

Figure 4:
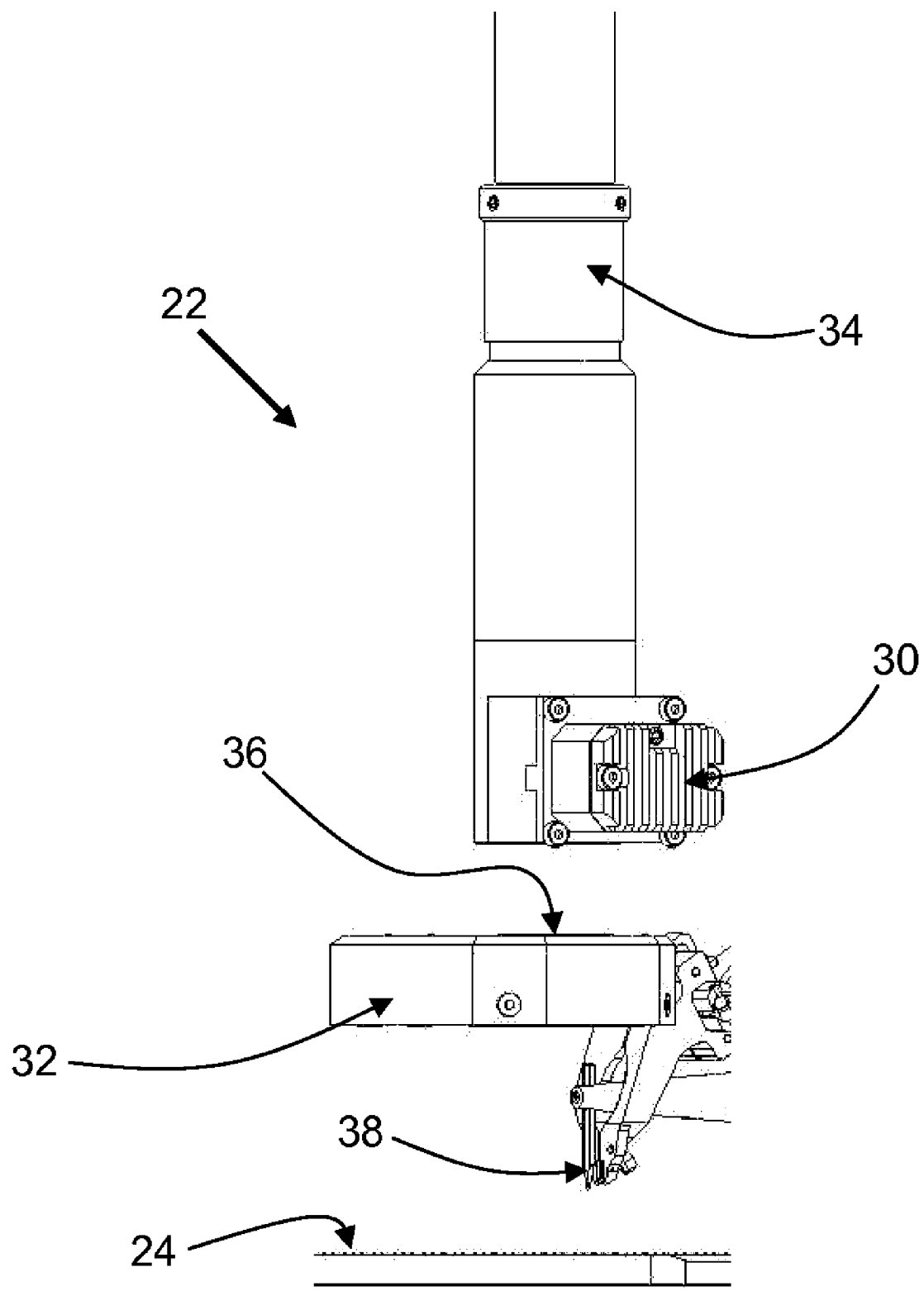
FIG. 4 is a side view of the wire bonding apparatus of FIG. 3.

FIG. 4 is a side view of the wire bonding apparatus of FIG. 3. The coaxial lighting source 30 projects coaxial light in a direction that is substantially parallel to the plane of the substrate 24. Thus, it is preferable to arrange a beam splitter (not shown) adjacent to the coaxial lighting source 30 to project the coaxial lighting onto the substrate 24 through the hole 36 in the ring lighting source 32. Light reflected from the surface of the substrate 24 passes through the hole 36 towards the CCD camera 34 for image-grabbing.

Figure 5:
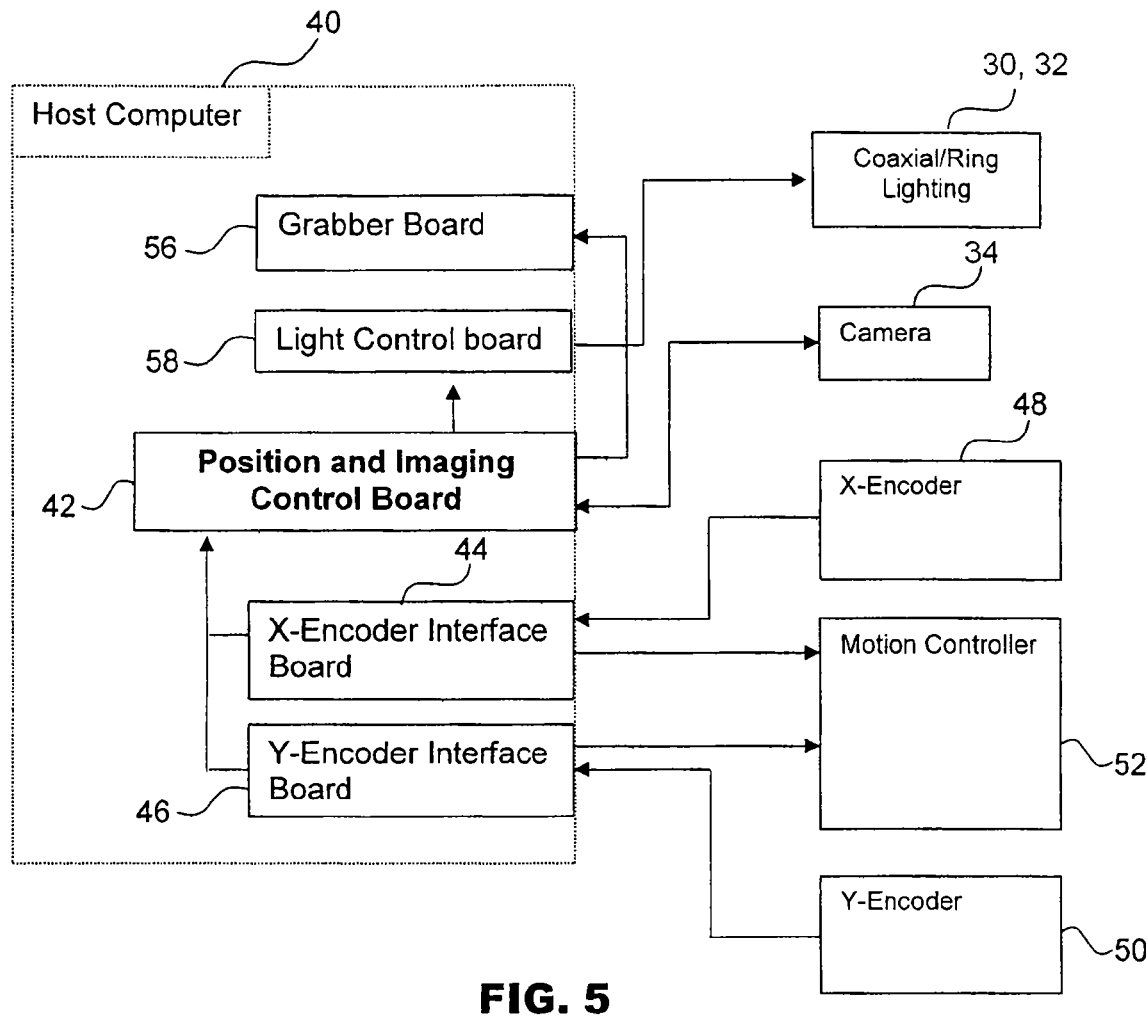
FIG. 5 is a block diagram showing the main components of the PR alignment apparatus according to the preferred embodiment of the present invention.

FIG. 5 is a block diagram showing the main components of the PR alignment apparatus according to the preferred embodiment of the present invention. The PR alignment apparatus is generally controlled by a host computer 40. The host computer 40 controls a position and imaging control board 42 which is responsible for synchronization between relative movement of the positioning stage and image capturing by the vision system at predetermined positions. The position and imaging control board 42 receives positional feedback regarding a position of the electronic device from an encoder assembly, preferably an X-encoder interface board 44 and/or a Y-encoder interface board 46, which obtain measurements from an X-encoder 48 and/or a Y-encoder 50 respectively. These monitor the X and Y positions of X and Y motors driving the XY table. The host computer 40 also transmits commands to a motion controller 52 of the XY table to move the substrate 24 mounted on the worktable 26.

When the position and imaging control board 42 detects that the camera 34 of the vision system is over a target position, it will activate the camera 34 to start exposure to view the target position and a grabber board 56 to acquire an image of the target position. At the same time, it also triggers a light control board 58 so that the coaxial lighting source 30 and ring lighting source 32 illuminate the target position of the substrate 24 with the necessary lighting intensity during image capture. All the above are performed while the electronic device is undergoing relative motion with respect to the vision system without stopping.

As the positioning stage is preferably programmed to move at a substantially uniform velocity along a motion path without stopping when the vision system is performing image capturing of a plurality of target positions, and more preferably at the highest speed that the positioning stage is configured to operate, the host computer 40 will provide pre-stored coordinates of a number of bonding positions to be aligned, whereat the images are to be acquired. The encoder positions at these coordinates are used as trigger positions.

At the target positions as detected by the X-encoder 48 and/or Y-encoder 50, the position and imaging control board 42 will activate the camera 34 and co-axial and ring lighting source 30, 32 simultaneously to grab an image while the substrate 24 is still in motion. Other than using the encoder positions to trigger image capturing, image capturing can also be activated through separate commands from the host computer 40 as with conventional PR alignment methods which would generally require that motion of the electronic device be stopped, but the exposure time may still be advantageously shorter because the camera 34 has a shorter exposure time.

To achieve the above PR alignment method, a faster camera with a shorter exposure time and lighting source with a higher intensity would thus be necessary as compared to the prior art. Preferably, the exposure time of the camera 34 is less than 1 millisecond and more preferably, less than 20 microseconds. The intensity of light generated by the coaxial/ring lighting source 30, 32 is preferably more than thirty times the light intensity that is conventionally used. As such, pulse lighting is preferred in order to overdrive the lighting sources to produce a very high light intensity for a very short period of time, for a duration that is sufficient to illuminate the target position for the duration of the exposure time. Nevertheless, it should be appreciated that the exposure time of the camera 54 and light intensity used are related to the motion speed of the electronic device. Higher motion speeds would require a shorter exposure time whereas cameras with longer exposure times may be used if motion speed is lower. Similarly, the required light intensity depends on the exposure time. Higher instantaneous light intensities are required for shorter exposure times. Furthermore, the light intensity can further be lowered by using a higher gain camera.

The above features allow the camera 34 to be located above multiple bonding positions to be aligned while the positioning stage is moving the electronic device at full speed without stopping. Hence, the camera 34 is able to capture images of the bonding positions on-the-fly without sacrificing alignment accuracy. Since the worktable 26 is in constant motion, the image capture time for a point is reduced to the exposure time of the camera 34, which may be less than 20 microseconds. Moreover, since the exposure time is negligible, the capturing time for an image will in practice be limited more by the image transfer time (which is relatively longer), and less by the camera exposure time or the table motion time during the image capture process.

Figure 6:
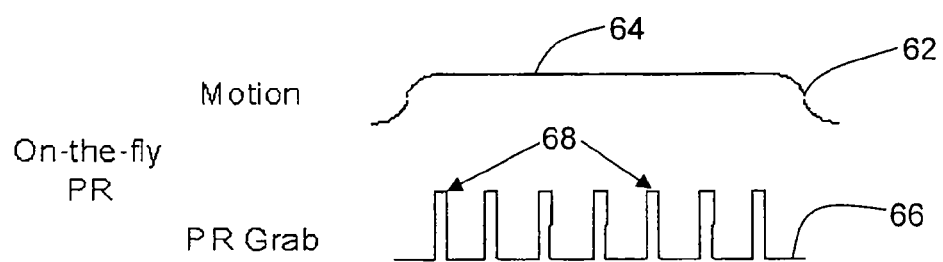
FIG. 6 is an illustration of an exemplary motion sequence showing the points at which PR image-grabbing is performed in the PR alignment system according to the preferred embodiment.

FIG. 6 is an illustration of an exemplary motion sequence showing the points at which PR image-grabbing is performed in the PR alignment system according to the preferred embodiment. From the velocity-time graph 62, it can be seen that the positioning stage accelerates the electronic device from rest to a substantially constant speed 64 during which the vision system is operative to view a series of bonding positions. Preferably, this is the highest speed at which the positioning stage is configured to operate. According to PR grabbing graph 66, a series of PR grabs 68 can be performed without having to slow down or stop the movement of the electronic device. This results in significant time savings.

Figure 7:
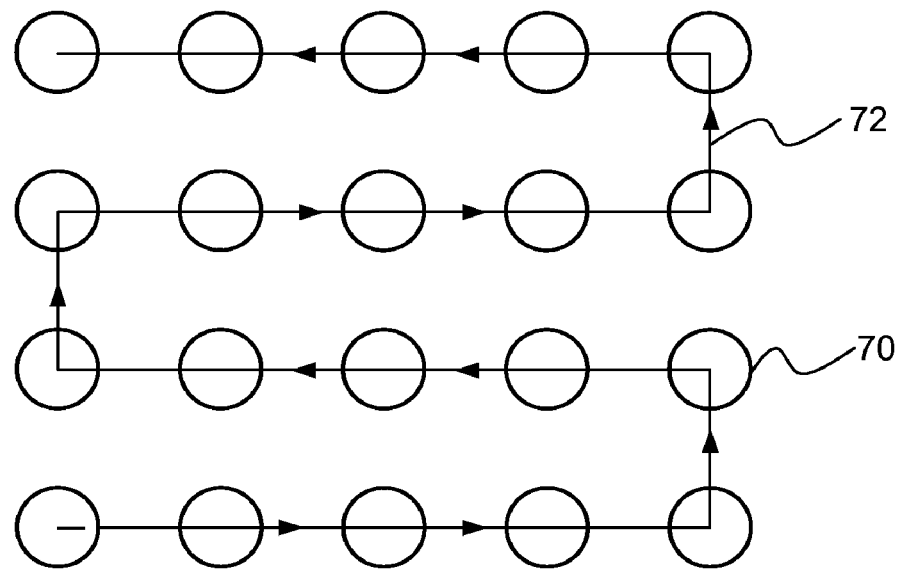
FIG. 7 is an illustration of the PR alignment method according to the preferred embodiment wherein LED bonding points arranged in matrix form are moved relative to an image-grabbing camera.

FIG. 7 is an illustration of the PR alignment method according to the preferred embodiment wherein LED bonding points 70 arranged in matrix form are moved relative to an image-grabbing camera. Motion path 72 shows the direction of movement of the positioning stage/electronic device. It can be appreciated that for each row of LED bonding points 70, the positioning stage may move the electronic device at full speed relative to the vision system on that row, after which it will decelerate in that direction in order to move the vision system to grab images of another row, and so on. Hence, the positioning stage needs only to stop the electronic device moving in a particular direction at the end of each row instead of at each and every LED bonding point. This saves a lot of time in not having to accelerate and decelerate between each and every LED bonding point.

Figure 8:
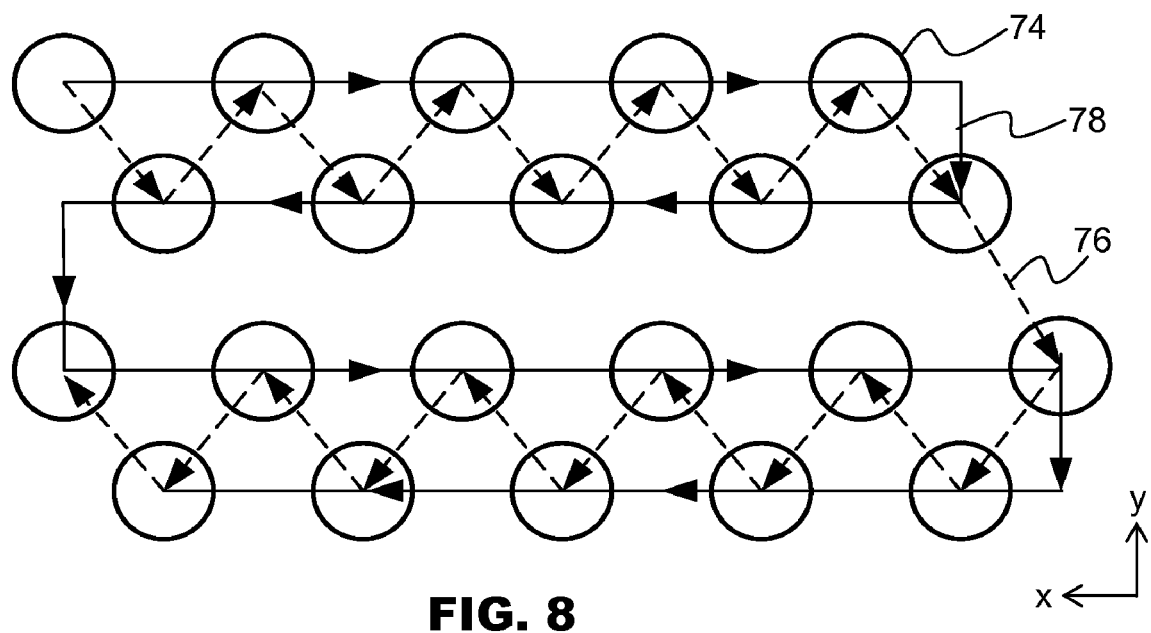
FIG. 8 illustrates how PR alignment may be performed using a prior art method as compared to the method according to the preferred embodiment for LED bonding points that are arranged relative to one another in a staggered fashion.

FIG. 8 illustrates how PR alignment may be performed using a prior art method as compared to the method according to the preferred embodiment for LED bonding points 74 that are arranged relative to one another in a staggered fashion. Motion path 76 shows a prior art method of traversing the various staggered LED bonding points 74. Using the prior art method of stopping at each LED bonding point 74 to grab an image, it would be typical to move between the rows of LED bonding points 74 diagonally since that represents the shortest distance between adjacent LED bonding points 74.

If the PR method according to the invention were to adopt the same motion path 76, this would still involve acceleration and deceleration by the positioning stage to move between LED bonding points because the motions involve changes in direction in the Y axis. However, motion path 78 shows how the motion path can be further enhanced using the improved method. Instead of moving the electronic device diagonally which would involve acceleration and deceleration in the Y axis for each LED bonding point 74, it would be possible to modify the motion path to travel through the lengths of each row of LED bonding points 74 at a time. Accordingly, acceleration and deceleration for LED bonding points 74 located on the same row is minimized. Therefore, not only are there savings in time by not having to stop at every LED bonding point 74, a more efficient motion path 78 can be selected which further minimizes the need for acceleration and deceleration of the positioning stage to further increase PR alignment speed.

Apart from the application of the PR alignment apparatus and method to wire bonding and other types of bonding during semiconductor assembly and packaging, the described apparatus and method can also be used in other applications such as a Visual Lead Locator function for locating the centers of all leads on a leadframe and auto die pad centering to locate the centers of each die pad on a die. Moreover, post-bond inspection can also be conducted such that the pattern that is recognized is an image of the bonded material. This may be used to distinguish the bond quality of the bonded material during post-bond quality control. Conventionally, these operations are time-consuming and it may therefore not be practical to perform them in most circumstances. With the apparatus and method according to the preferred embodiment of the invention, the inspection time is much shorter, and it would thus be more practical to perform them to improve bonding accuracy and device quality.

Figure 9:
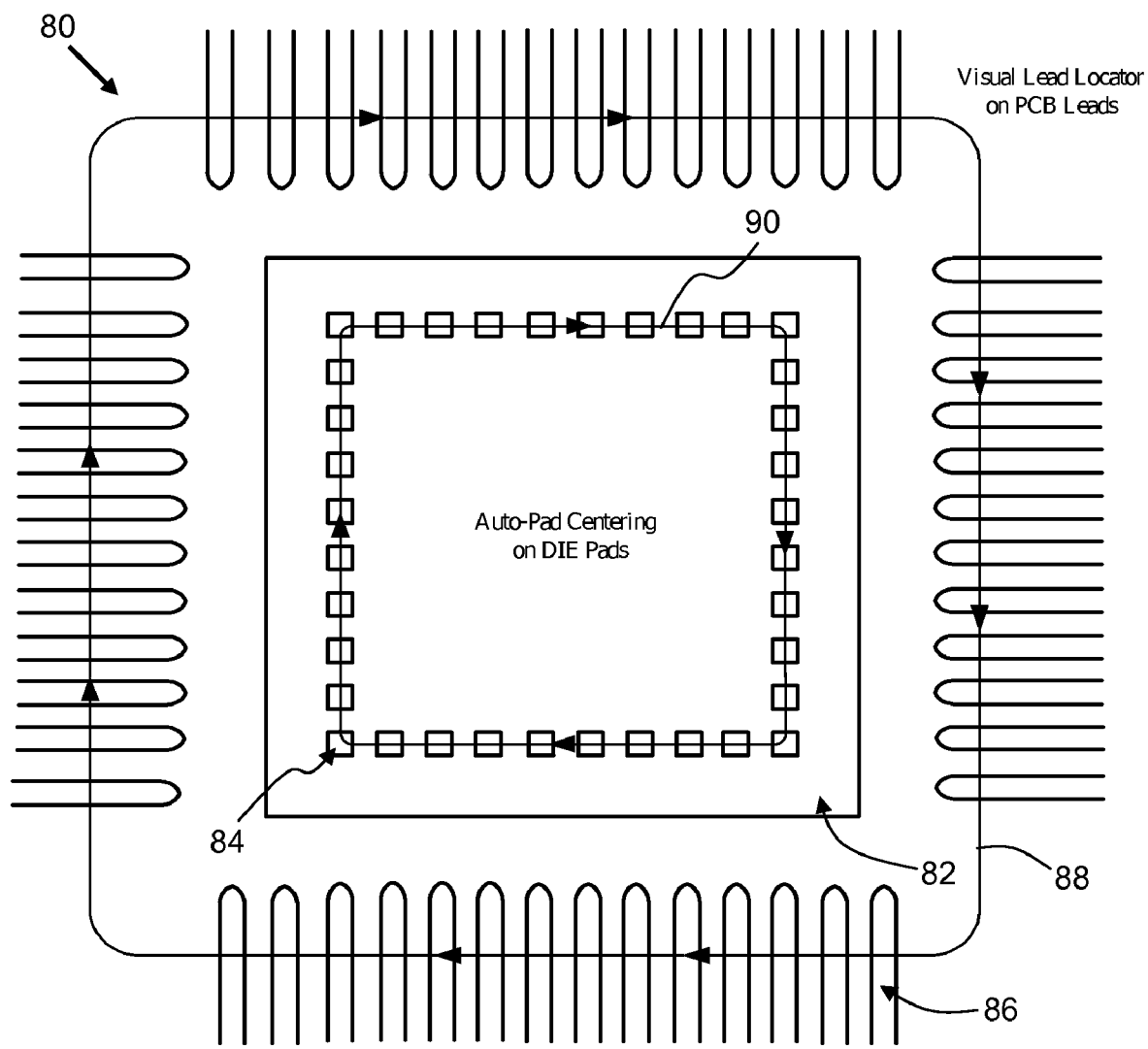
FIG. 9 is an illustration of the PR alignment method according to the preferred embodiment as applied to a leadframe device.

FIG. 9 is an illustration of the PR alignment method according to the preferred embodiment as applied to a leadframe device 80. The leadframe device 80 has a die 82 mounted on it, and the die 82 has multiple bond pads 84 used for bonding. The bond pads 84 should be electrically connected to the leads 86 by bonding conductive wires therebetween. To facilitate wire bonding, the vision system can be moved along motion path 88 to capture images of each lead 86 to locate the centers of all leads 86 on the leadframe 80. Furthermore, the vision system can be moved along motion path 90 to capture images of the bond pads 84 in order to locate the centers of all bond pads 84 on the die 82.

It should be appreciated that the PR alignment apparatus and method according to the preferred embodiment of the invention serves to greatly reduce PR alignment time as compared to the aforesaid prior art. Consequently, productivity of the bonding apparatus is improved because PR alignment generally takes up a significant portion of bonding time.

The invention described herein is susceptible to variations, modifications and/or additions other than those specifically described and it is to be understood that the invention includes all such variations, modifications and/or additions which fall within the spirit and scope of the above description.

The invention claimed is:

1. An image capturing method for pattern recognition of a plurality of target positions on an electronic device to align the plurality of target positions, comprising the steps of:

mounting the electronic device on a positioning stage;

pre-storing coordinates of the plurality of target positions to be aligned;

moving the electronic device by the positioning stage relative to a vision system at a uniform velocity for positioning the vision system over the plurality of target positions on the electronic device;

while moving the electronic device at the uniform velocity, determining when the vision system is positioned over each of the coordinates of the target positions to view the target position on the electronic device; and capturing an image of each of the target positions on the electronic device with the vision system while the electronic device is undergoing relative motion with respect to the vision system at the uniform velocity without stopping; and using the images of the target positions to align the target positions.

2. The image capturing method as claimed in claim 1, wherein the step of capturing an image of each of the target positions is triggered by a position and imaging control board that is operative to synchronize relative movement of the electronic device and image capturing by the vision system.

3. The image capturing method as claimed in claim 2, wherein the step of determining when the vision system is positioned over each of the coordinates of the target positions further comprises the position and imaging control board receiving positional feedback from an encoder regarding a position of the electronic device.

4. The image capturing method as claimed in claim 2, wherein the step of capturing an image of each of the target positions further comprises the steps of utilizing the position and imaging control board to:
  activate a light source to illuminate the target position with high intensity lighting;
  activate a camera to view the target position; and
  activate a grabber board to acquire an image of the target position.

5. The image capturing method as claimed in claim 1, wherein the uniform velocity is a highest speed at which a positioning stage on which the electronic device is mounted is configured to operate.

6. The image capturing method as claimed in claim 1, wherein the vision system comprises a high intensity lighting source and a CCD camera connected to an image grabber board.

7. The image capturing method as claimed in claim 6, wherein the lighting source comprises pulse lighting.

8. The image capturing method as claimed in claim 7, wherein the lighting source comprises a coaxial lighting source and a ring lighting source.

9. The image capturing method as claimed in claim 6, wherein the CCD camera has an exposure time of less than 1 millisecond.

10. The image capturing method as claimed in claim 1, wherein the pattern that is recognized is an image of material that has been bonded so as to distinguish bonding quality of the bonded material.

11. An apparatus for capturing an image for pattern recognition of a plurality of target positions on an electronic device to align the plurality of target positions, comprising:
  a device that is configured to pre-store coordinates of the plurality of target positions to be aligned;
  a vision system for capturing images of the electronic device; and
  a positioning stage on which is mounted the electronic device, the positioning stage being configured to move the electronic device at a uniform velocity relative to the vision system in order for the vision system to view each of the plurality of target positions on the electronic device;
  wherein the vision system is configured to capture an image of each of the target positions on the electronic device when the vision system is positioned over each of the respective coordinates of the target positions and while the electronic device is undergoing relative motion with respect to the vision system at the uniform velocity without stopping, whereby to align the target positions.

12. The apparatus as claimed in claim 11, further comprising a position and imaging control board that is configured to synchronize relative movement of the electronic device and image capturing by the vision system.

13. The apparatus as claimed in claim 12, further comprising an encoder for providing positional feedback to the position and imaging control board regarding a position of the electronic device for determining when the vision system is positioned over each of the respective coordinates of the target positions on the electronic device.

14. The apparatus as claimed in claim 11, wherein the uniform velocity is a highest speed at which the positioning stage is configured to operate.

15. The apparatus as claimed in claim 11, wherein the vision system comprises a high intensity lighting source and a CCD camera connected to an image grabber board.

16. The apparatus as claimed in claim 15, wherein the lighting source comprises pulse lighting.

17. The apparatus as claimed in claim 16, wherein the lighting source comprises a coaxial lighting source and a ring lighting source.

18. The apparatus as claimed in claim 15, wherein the CCD camera has an exposure time of less than 1 millisecond.

19. An apparatus for capturing an image for pattern recognition of a plurality of target positions on an electronic device to align the plurality of target positions, comprising:
  a device that is configured to pre-store coordinates of a target position to be aligned;
  a vision system for capturing images of the electronic device; and
  a positioning stage on which is mounted the electronic device, the positioning stage being configured to move the electronic device relative to the vision system in order for the vision system to view each of the plurality of target positions on the electronic device;
  wherein the vision system is configured to capture an image of each of the target positions on the electronic device when the vision system is positioned over each of the respective coordinates of the target positions and while the electronic device is undergoing relative motion with respect to the vision system without stopping, whereby to align the target positions.

* * * * *